United States Patent
Blanchard

(10) Patent No.: US 6,171,426 B1
(45) Date of Patent: Jan. 9, 2001

(54) METHOD OF MAKING A COATED TAMPON APPLICATOR

(75) Inventor: Stephen J. Blanchard, North Brunswick, NJ (US)

(73) Assignee: McNeill-PPC, Inc., Skillman, NJ (US)

(*) Notice: Under 35 U.S.C. 154(b), the term of this patent shall be extended for 0 days.

(21) Appl. No.: 09/105,787

(22) Filed: Jun. 26, 1998

(51) Int. Cl.[7] .................. B39C 53/00; B39C 45/00; A61F 13/20; B05D 3/12
(52) U.S. Cl. ................. 156/203; 156/218; 156/466; 264/512; 427/179; 427/293; 427/2.3; 604/15
(58) Field of Search .................. 604/11–18, 904; 264/510, 512, 563, 564, 544, 545; 156/203, 466, 217, 218; 427/2.3, 2.31, 179, 293, 398.1, 401

(56) References Cited

U.S. PATENT DOCUMENTS

| | | | |
|---|---|---|---|
| 2,210,436 | * 8/1940 | Weingand et al. | 156/203 |
| 3,411,542 | * 11/1968 | Walsh et al. | 156/466 |
| 3,581,744 | * 6/1971 | Voss | 604/14 |
| 4,412,833 | 11/1983 | Wiegner et al. | 604/14 |
| 4,508,531 | * 4/1985 | Whitehead | 604/15 |
| 4,622,030 | * 11/1986 | Sheldon | 604/15 |
| 4,755,164 | * 7/1988 | Hinzmann | 156/203 |
| 5,002,526 | 3/1991 | Herring | 604/11 |
| 5,100,496 | * 3/1992 | Mitchell | 156/446 |
| 5,346,468 | * 9/1994 | Campion et al. | 604/13 |
| 5,389,068 | 2/1995 | Keck | 604/15 |
| 5,547,701 | 8/1996 | Nielsen et al. | 427/2.3 |
| 5,702,553 | * 12/1997 | Iskra et al. | 156/203 |
| 5,709,652 | 1/1998 | Hagerty | 604/15 |
| 5,873,971 | * 2/1999 | Balzar | 156/217 |

* cited by examiner

Primary Examiner—Dennis Ruhl

(57) ABSTRACT

A tampon applicator member can be made from a roll of sheet-like material. A flowable material is applied to one surface of the sheet-like material and is transformed into a solid polymeric layer. The coated material is separated into a plurality of applicator blanks. A first surface of each blank, corresponding to the first surface of the individual sheet-like web, has an uncoated portion adjacent a first side edge, parallel to the longitudinal axis, and a coated portion. An adhesive is applied to the uncoated portion of the first surface of a blank, and the blank is rolled to form a tubular member having a longitudinal seam. The seam has a first edge of the inner surface of the structural member superposed over and adhered to an uncoated opposite edge of the outer surface of the structural member.

11 Claims, 3 Drawing Sheets

METHOD OF MAKING A COATED TAMPON APPLICATOR

FIELD OF THE INVENTION

The present invention relates to a method of making a tampon applicator having a polymeric coating and to tampon applicators made therefrom. In particular, the present invention discloses a method of making a longitudinally seamed tampon applicator from a substrate that is partially coated on its outwardly facing surface.

BACKGROUND OF THE INVENTION

Tampon applicators are typically fabricated from either cardboard or plastic materials, with both capable of having laminates or coatings thereon. Plastic applicators are generally associated with easy and comfortable insertion into the body, especially on light flow days. However, the currently marketed plastic products are constructed from polyolefins, and these materials are not considered flushable or degradable. Thus, they are not generally considered to be safe for the environment. There has been considerable research performed on water-dispersible and degradable polymers to eliminate these deficiencies, but many of the approaches compromise the properties that make plastic applicators attractive to consumers, such as perceived surface smoothness. The degradable materials can also be significantly more expensive than traditional polyolefins, making them uneconomical. Herring, U.S. Pat. No. 5,002,526 discloses a water-soluble plastic applicator made from polyvinyl alcohol based compositions. Another approach using water-dispersible polyesters to improve flushability of applicators is disclosed in Keck, U.S. Pat. No. 5,389,068.

Conversely, cardboard applicators are generally considered to be more environmentally friendly and more easily and discreetly disposable, because they are generally flushable in standard toilets. However, some consumers do not believe that cardboard applicators are as easy and comfortable to insert as plastic applicators, due to the differences in their respective surfaces.

In an effort to provide the consumer with the attractive properties of both applicator types, products have been designed and marketed that contain thin polymeric films laminated to cardboard substrates. An example of this approach is disclosed in Campion et al., U.S. Pat. No. 5,346,468. This reference also describes spirally wound tubes. Other tampon applicators are formed of convolutely wound tubes as described in Whitehead, U.S. Pat. No. 4,508,531.

A third known method of fabricating a cardboard tube, is disclosed in Hinzmann, U.S. Pat. No. 4,755,164. This patent disclosed forming a cylindrical tube from a rectangular sheet of pre-cut material. The method requires overlapping a portion of the two longitudinal edges of the rectangular sheet, to form a longitudinal seam. While this fabrication method is useful in cardboard or paperboard applicators, it is more difficult to employ this method to form applicators having an outer layer of plastic. This is because the longitudinal seam is likely to be weaker if the plastic layer is present in the seam area. Thus, the seam adhesive would not be able to penetrate the cardboard structure by both mechanical and chemical bonding, in comparison to a simple cardboard material. Thus, the seam area should be free of the plastic layer to form as strong a seam as possible. This strength is required, because tampons contained within these applicators may be radially-expanding tampons that may exert a significant "hoop stress" on the seam prior to the expulsion of the tampon out of the applicator. If the hoop stress overcomes the seam bond strength, then the seam can open up and cause discomfort during insertion, or alternatively be unusable.

Therefore, what is needed is a method of forming an economical applicator for use with tampons that has a strong, longitudinal seam and a pleasingly smooth polymeric outer surface.

SUMMARY OF THE INVENTION

A tampon applicator member can be made from a roll of sheet-like material. A rolled sheet-like material having a first surface and a second surface is unwound, and a flowable material is applied to the first surface of the sheet-like material to form a plurality of discrete coated zones. The flowable material can be transformed into a solid polymeric layer in the discrete coated zones. A plurality of individual, sheet-like webs of coated material can be slit from a master roll. A first surface of each individual web, corresponding to the first surface of the sheet-like material, has an uncoated portion adjacent a first side edge, and a coated portion. An individual web is then separated into a plurality of applicator blanks, having a longitudinal axis that is substantially greater than a transverse axis. A first surface of each blank, corresponding to the first surface of the individual sheet-like web, has an uncoated portion adjacent a first side edge, parallel to the longitudinal axis, and a coated portion. An adhesive is applied to the uncoated portion of the first surface of a blank, and the blank is formed around a forming mandrel that is oriented parallel to the longitudinal axis of the blank, leaving the first surface outwardly disposed. A second side edge of the blank, opposite the first side edge, is superposed over the first side edge to substantially overlap the uncoated portion of the first surface of the blank and to adhere the second surface of the blank, corresponding to the second surface of the sheet-like web, to the first surface of the blank to form a longitudinal seam, thereby forming the applicator member having an exposed, outwardly disposed surface.

The invention also relates to a longitudinally-seamed tampon applicator. The member has a tubular structural member having an outer surface that is substantially coated with a solid polymeric layer. The longitudinal seam has a first edge of the inner surface of the structural member superposed over and adhered to an uncoated opposite edge of the outer surface of the structural member.

BRIEF DESCRIPTION OF THE INVENTION

DETAILED DESCRIPTION OF THE INVENTION

Figure 1:
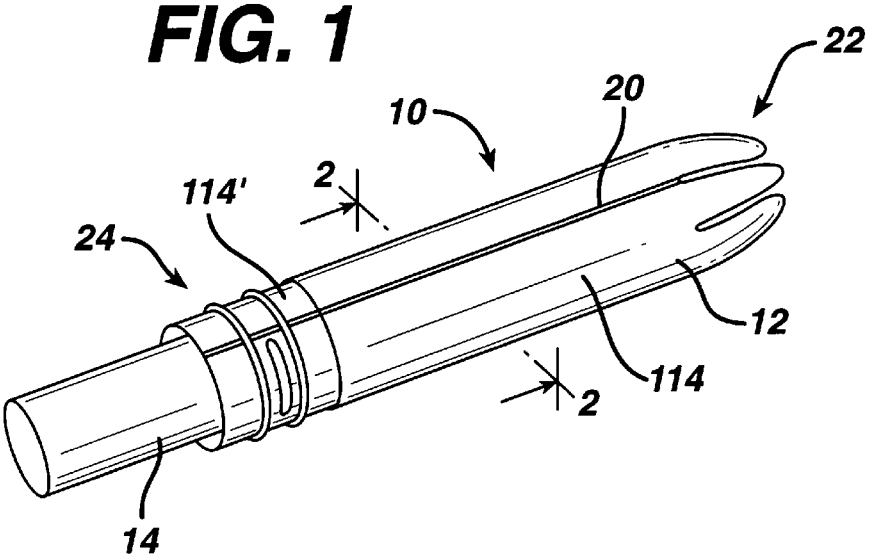
FIG. 1 represents a perspective view of a tampon applicator according to the present invention.
Figure 2A:
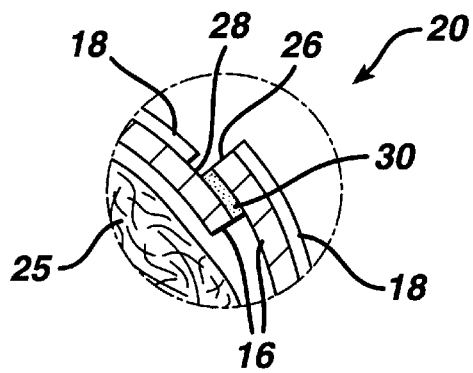
FIG. 2a represents an enlarged view of the longitudinal seam of FIG. 2.
Figure 2:
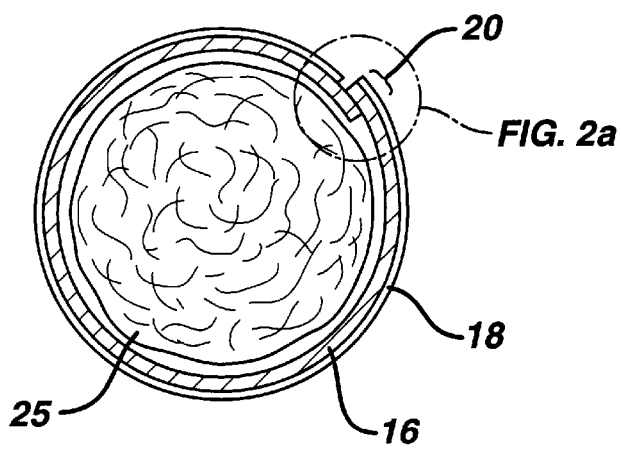
FIG. 2 represents a cross-section along line 2—2 of FIG. 1.

A tampon applicator 10 having barrel 12 and a telescopically moveable plunger 14 is disclosed in FIGS. 1 and 2. At least the barrel 12 is formed of a structural member 16, an outer polymeric surface 18, and a longitudinal seam 20. The barrel 12 may have additional elements such as a domed expulsion end 22, and an enhanced gripper end 24. The tampon applicator 10 is configured to contain a tampon 25 within the barrel 12.

Figure 3A:
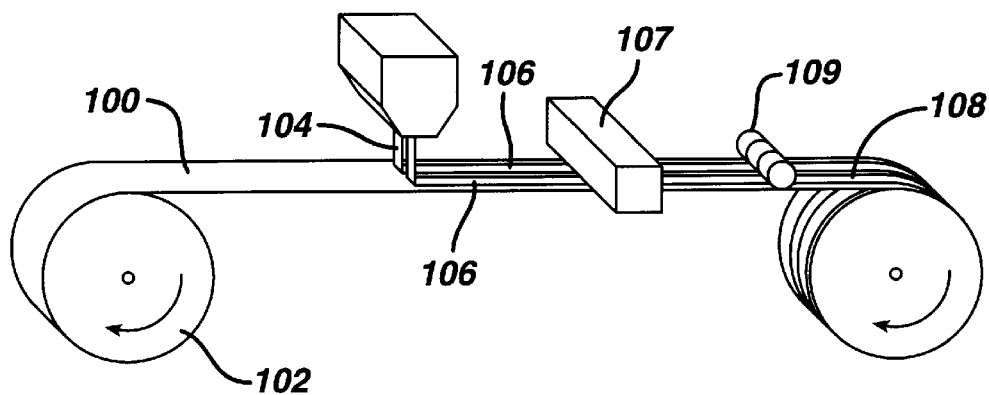
FIGS. 3a and 3b represent the process of the present invention.
Figure 3B:
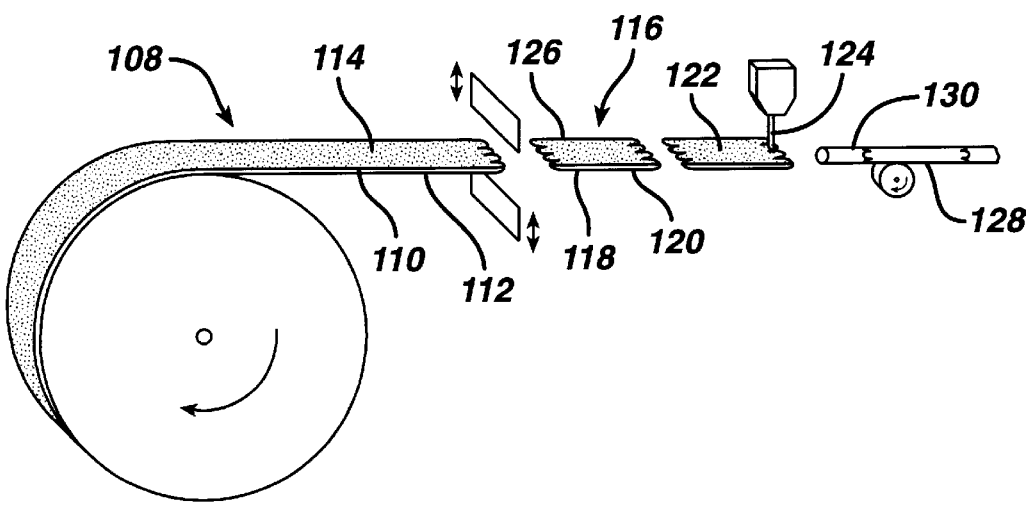

The longitudinal seam 20 is shown in greater detail in FIG. 2a. The longitudinal seam 20 is formed generally by superposing or overlapping a first edge 26 of the structural member 16 over the opposite uncoated edge 28 of the structural member. The first edge 26 is then adhered to the uncoated portion of the opposite edge 28. This may be done through an adhesive substance 30. A preferred process of making at least the barrel 12 of this tampon applicator 10 is illustrated in FIGS. 3a and 3b. In this process, a rolled, sheet-like material 100 is unwound from a supply 102. The sheet-like material 100 has a width and a length that is substantially greater than the width; in a roll form, the length is substantially infinite. The sheet-like material 100 becomes the structural member 16 in the finished applicator 10. A representative, non-limiting list of materials useful as the sheet-like material 100 includes cellulosic materials such as paper, paperboard, cardboard, and the like and polymeric materials such as polyolefins, polyesters, polyurethanes, polyamides, acetates, polyvinyl alcohol, ethylene-vinyl acetate, cellulose acetate, polymeric starch, and the like. Preferably the sheet-like material 100 is cellulosic in nature, to provide the attractive disposability and structural characteristics. Most preferably, the cellulosic material is paperboard or cardboard.

Applicators are designed to possess sufficient structurally stability to allow the user to comfortably insert it a body cavity and expel the enclosed tampon without collapse of the applicator. One indicator of the strength of the sheet-like material 100 is its basis weight. This is particularly valid in the cellulosic materials. Preferably, the basis weight of the cellulosic material is from about 30 to about 350 grams per square meter. More preferably, it is from about 100 to about 300 grams per square meter, and most preferably, it is about 200 to about 300 grams per square meter.

The first surface of the sheet-like material 100 can also be treated to improve the bond strength between it and the polymeric films applied thereto. Mechanical treatment, such as skiving, can increase the surface area, thereby increasing the bond strength. Chemical treatments known to a person skilled in the art to improve adherence of two materials can be incorporated to improve the present invention. Chemical treatments can include both chemical alterations to the surfaces and added chemical coupling agents. Corona treatment is known to increase the surface energy and improve wettability of polar adhesives. Coupling agents are designed to have bifunctional groups, with each functional group chemically reacting with the respective materials to be bonded. In addition, the surface may be treated to limit the absorption characteristics of the substrate if the flowable material is liquid. For example, a clay-coated cardboard may be used.

A flowable, material 104 is applied to the to sheet-like material 100 in a manner to form a plurality of discrete coated zones 106 on the first, upper surface thereof. A representative, non-limiting list of flowable materials 104 that are useful in the present invention includes, cellophane, polyester, polyethylene, polypropylene, epoxy, polyvinyl alcohol, acrylics, ethylene-vinyl acetate, polycarbonate, polyamides, such as nylon, polystyrene, hydroxy propyl methylcellulose, and the like. The flowable material may also be formulated with additional components including, without limitation, plasticizers, catalysts, curing agents, thermal stabilizers, pigments, fillers, fragrances, surfactants, lubricants, blooming agents, antimicrobial agents, medicaments, and the like. If the material, as formulated, is not inherently flowable, it may be made flowable, by adding a sufficient amount of energy to the material 104, prior to adding them to the sheet-like material 100. A known flowable material is a UV curable, clear epoxy protective coating, PAD-KOTE K261, available from Rad-Cure Corp., Fairfield, N.J., USA.

There are many techniques known for applying the polymeric material 104. A representative, non-limiting list of such processes includes powder coating, spraying, extruding, slot-coating, brushing, transfer coating, and the like. Preferably, the polymeric material 104 is applied using multiple slot coat heads and/or a multiroll transfer process. The polymeric material 104 is then transformed into a solid polymeric layer. This can be achieved by known processes including, without limitation, drying, curing (including radio frequency, ultraviolet energy, and electron beam), melting, fusing, chilling, and the like, for example at curing station 107.

It is preferred that the edge of the discrete coated zones 106 be maintained with tight tolerances to keep the seam forming portion of the sheet-like material 100 free from the coating material. Preferably, the edge of the discrete coated zones 106 are maintained within a tolerance of +/−3 mm, more preferably, within a tolerance of +/−2 mm. This can be achieved on a commercial scale by forming conventional transfer coating rolls using conventional lathe machining process. Other edge control techniques will be apparent to those who are skilled in the art.

More than one polymeric coating can be applied. The multiple coatings can serve both aesthetic and functional purposes. The first polymeric coating could contain patterns or pigments that would be visible through subsequent polymeric coatings. The outermost polymeric coating could also have extremely low dry and wet frictional properties, to facilitate easy and comfortable insertion into body cavities.

Figure 4:
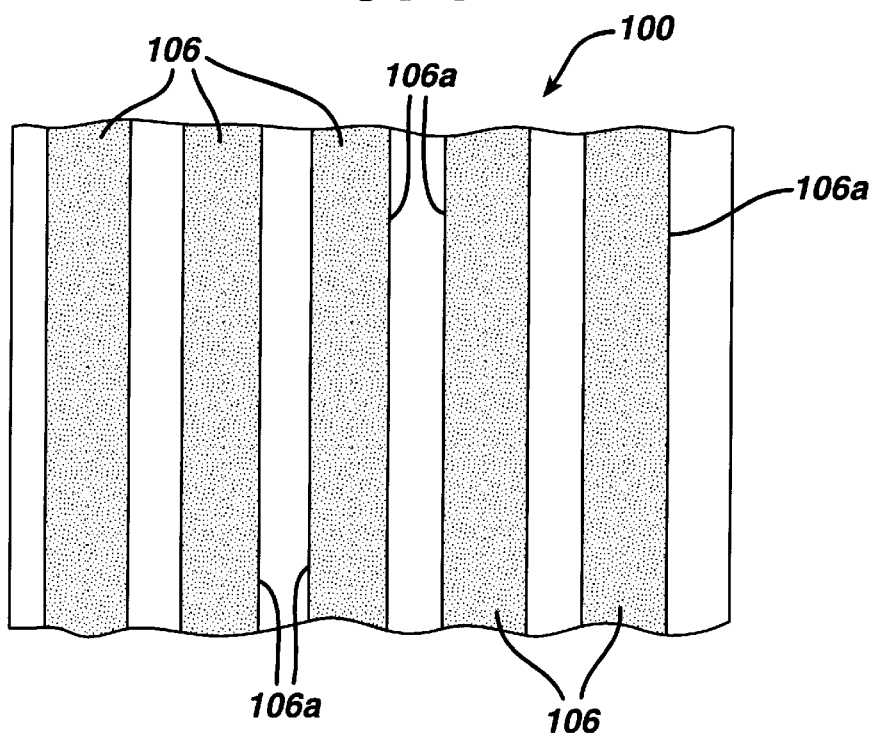
FIG. 4 represents a drawing of the sheet-like material and one design of the plurality of discrete coated zones.

If the sheet-like material 100 is wider than necessary to form individual tampon applicators, as shown in FIG. 4, it can be slit into a number of individual sheet-like webs of material 108. These first surface of the webs 108, corresponding to the first surface of the sheet-like material 100, has an uncoated portion 110 adjacent a first side edge 112 and a coated portion 114.

Figure 5:
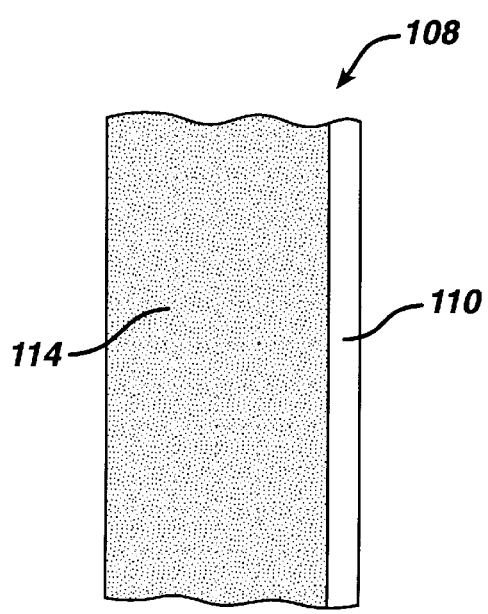
FIG. 5 represents an embodiment of the individual sheet-like web and its coated portion.
Figure 6:
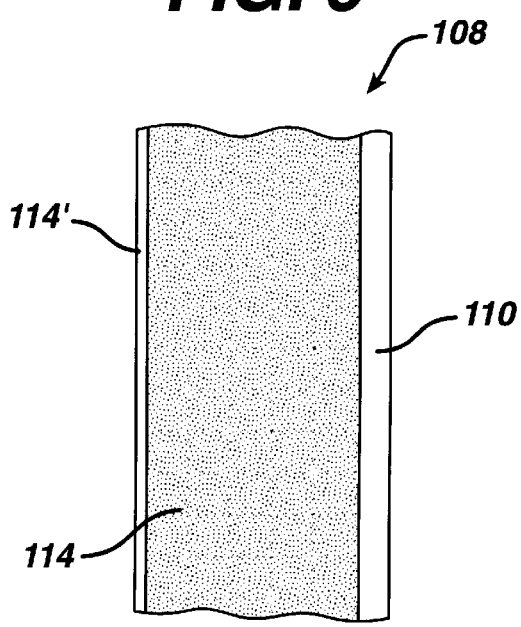
FIG. 6 represents another embodiment of the individual sheet-like web and its coated portion.

The coated portion 114 may have one or more void areas 114' disposed away from the uncoated edge 110. These void areas may have a number of uses recognized by a skilled practitioner, e.g., to increase surface roughness in the gripper end 24 of the tampon applicator barrel as shown in FIG. 1. The present invention can also employ multiple slit designs that will result in individual slit webs 108 containing the coated portion 114 in various locations. FIGS. 5 and 6 illustrate two individual webs 108, either after slitting or as formed in a single line. The individual webs 108 can then be taken up in roll form in a conventional roll goods slitting apparatus 109.

An individual web 108 can then be placed onto equipment for manufacturing tampon applicators. One such piece of equipment is commercially available from Hauni Richmond, Inc. located in Richmond, Va. The operation of this equipment is generally described in Hinzmann, U.S. Pat. No. 4,755,164, the disclosure of which is hereby incorporated by reference. The individual web 108 can be unrolled and separated into a plurality of applicator blanks 116, each blank having a longitudinal axis which is substantially greater than its transverse axis and a first surface corresponding to the first surface of the web 108. Again, the blanks 116 have an uncoated portion 118 adjacent a first side edge 120 and a coated portion 122. If the uncoated portion 118 is too narrow, insufficient seam strength will result, if the uncoated portion 118 is too wide, a large uncoated strip may be objectionable to the user and may increase insertion and withdrawal forces. Preferably, the uncoated portion 118 adjacent the first side edge 120 is at least about 2 mm. The blanks 116 may be single blanks and formed into individual tampon applicator members or they can be double blanks that are then formed into double members to be separated at a later stage into individual members.

An adhesive material 124 can then be applied to the uncoated portion 118 of the blanks 116. The adhesive application will be rapidly followed by superposing a second side edge 126, opposite the first side edge 120, of the blank 116 over the first side edge 120 to substantially overlap the uncoated portion 118. The overlapping of the second side edge 126 over the first side edge 120 and subsequent sealing of the respective surfaces forms a longitudinal seam 128. This seam formation may take place around a forming mandrel 130 or similar forming member. The first surface of the blank 116 is oriented outwardly, such that the exposed, outwardly disposed surface is substantially covered with the solid polymeric layer or coated portion 122.

Additional process steps may be incorporated, including dome forming and finger grip forming as disclosed in Hagerty, U.S. Pat. No. 5,709,652, and Iskra et al., U.S. Pat. No. 5,702,553, the disclosures of which are herein incorporated by reference.

The plunger 14 may be have a conventional clay-coated paperboard or cardboard outer surface or it may have the polymeric outer surface formed in a similar process to that described above. The barrel 12, plunger 14, and a tampon 26 can be assembled according to processes known to those ordinarily skilled in the art. The outside diameter of the plunger 14 is slightly less than the inside diameter of the barrel 12 to facilitate the telescopic arrangement therebetween.

The specification above is presented to aid in the complete and non-limiting understanding of the invention disclosed herein. Since many variations and embodiments of the invention can be made without departing from its spirit and scope, the invention resides in the claims hereinafter appended.

What is claimed is:

1. A method of making a tampon applicator member comprising the following steps:
   a) unwinding a rolled sheet-like material having a first surface and a second surface;
   b) applying a flowable material to the first surface of the sheet-like material to form a plurality of discrete coated zones;
   c) transforming the flowable material into a solid polymeric layer in the discrete coated zones;
   d) slitting the sheet-like material to form a plurality of individual sheet-like webs of material, wherein a first surface of each individual web, corresponding to the first surface of the sheet-like material, has an uncoated portion adjacent a first side edge, and a coated portion;
   f) separating an individual web into a plurality of applicator blanks, having a longitudinal axis which is substantially greater than a transverse axis and wherein a first surface of each blank, corresponding to the first surface of the individual sheet-like web, has an uncoated portion adjacent a first side edge, parallel to the longitudinal axis, and a coated portion;
   g) applying an adhesive to the uncoated portion of the first surface of an applicator blank;
   h) forming the applicator blank around a forming mandrel that is oriented parallel to the longitudinal axis of the blank, leaving the first surface outwardly disposed;
   i) superposing a second side edge of the applicator blank, opposite the first side edge, over the first side edge to substantially overlap the uncoated portion of the first surface of the blank and to adhere the second surface of the blank, corresponding to the second surface of the sheet-like web, to the first surface of the blank to form a longitudinal seam, thereby forming the applicator member having an exposed, outwardly disposed surface.

2. The method of claim 1 wherein the roll of sheet-like material is paperboard.

3. The method of claim 1 wherein the roll of sheet-like material is polymeric.

4. The method of claim 1 further comprising treating the first surface of the sheet-like material to improve adhesion of the solid polymeric layer.

5. The method of claim 4 wherein the treating step is chemical or mechanical.

6. The method of claim 1 wherein the solid polymeric coating is applied to the roll of sheet-like material, thereby forming a permanent bond between said solid polymeric layer and said roll of sheet-like material, in the absence of additional bonding materials.

7. The method of claim 1 wherein the outwardly disposed surface of the applicator member is substantially covered with the solid polymeric layer.

8. The method of claim 1 further comprising the step of applying an additional flowable material to the roll of sheet-like material.

9. The method of claim 1 wherein the solid polymeric layer comprises an epoxy, a polyolefin, a cellophane, a polyester, a polyvinyl alcohol, an acrylic, a polyamide, or a combination thereof.

10. The method of claim 1 wherein the uncoated portions have a border with the coated portions and the location of the border is controlled within about 3 mm.

11. A method of making a tampon applicator member comprising the following steps:
   a) unwinding a rolled sheet-like material having a longitudinal axis, a first surface, and a second surface;
   b) applying a flowable material to a portion of the first surface of the sheet-like material, wherein the sheet-like material has an uncoated portion adjacent a first side edge, parallel to the longitudinal axis, and a coated portion;
   c) transforming the flowable material into a solid coating layer;
   f) separating the sheet-like material into a plurality of applicator blanks, having a longitudinal axis, corresponding to the longitudinal axis of the sheet-like material, which is substantially greater than a transverse axis and wherein a first surface of each blank, corresponding to the first surface of the sheet-like material, has an uncoated portion adjacent a first side edge, parallel to the longitudinal axis, and a coated portion;
   g) applying an adhesive to the uncoated portion of the first surface of a blank;

h) forming the blank around a forming mandrel that is oriented parallel to the longitudinal axis of the blank, leaving the first surface outwardly disposed;

i) superposing a second side edge of the blank, opposite the first side edge, over the first side edge to substantially overlap the uncoated portion of the first surface of the blank and to adhere the second surface of the blank, corresponding to the second surface of the sheet-like material, to the first surface of the blank to form a longitudinal seam, thereby forming the applicator member having an exposed, outwardly disposed surface.

* * * * *